United States Patent

Fabo

[11] Patent Number: 5,540,922
[45] Date of Patent: Jul. 30, 1996

[54] ABSORBENT WOUND DRESSING

[75] Inventor: Tomas Fabo, Mölnlycke, Sweden

[73] Assignee: Molnlycke AB, Goteborg, Sweden

[21] Appl. No.: 302,874

[22] PCT Filed: Mar. 30, 1993

[86] PCT No.: PCT/SE93/00271

§ 371 Date: Sep. 14, 1994

§ 102(e) Date: Sep. 14, 1994

[87] PCT Pub. No.: WO93/19710

PCT Pub. Date: Oct. 14, 1993

[30] Foreign Application Priority Data

Mar. 30, 1992 [SE] Sweden .................................. 9200984

[51] Int. Cl.[6] ................................................. A01N 25/34
[52] U.S. Cl. ........................... 424/402; 424/443; 424/444; 424/445; 424/449
[58] Field of Search ..................... 424/402, 426, 424/443, 445, 446, 447, 448; 428/604; 604/304

[56] References Cited

U.S. PATENT DOCUMENTS

| | | | |
|---|---|---|---|
| 4,664,662 | 5/1987 | Webster | 604/369 |
| 4,928,681 | 5/1990 | Langston et al. | 602/58 |
| 4,957,795 | 9/1990 | Riedel | 428/74 |
| 5,340,363 | 8/1994 | Fabo | 604/304 |
| 5,352,508 | 10/1994 | Cheong | 428/264 |

FOREIGN PATENT DOCUMENTS

| | | |
|---|---|---|
| 0251810 | 1/1988 | European Pat. Off. . |
| 455466 | 7/1988 | Sweden . |

Primary Examiner—Thurman K. Page
Assistant Examiner—William E. Benston, Jr.
Attorney, Agent, or Firm—Young & Thompson

[57] ABSTRACT

An absorbent wound dressing having a layer of hydrophobic silicone gel (3) which is intended to lie against the wound surface when the dressing is worn. A layer of carrier material (2; 7) carries the gel layer and affords the requisite strength thereto. An absorbent body (5) is placed on that side of the carrier material and gel layer which lie distal from the wound surface in use. The carrier material and the gel layer have mutually coinciding penetrating perforations (4) at least within the region of the absorbent body. A fluid barrier layer (6) is provided on that side of the dressing which lies distal from the wound surface in use.

6 Claims, 1 Drawing Sheet

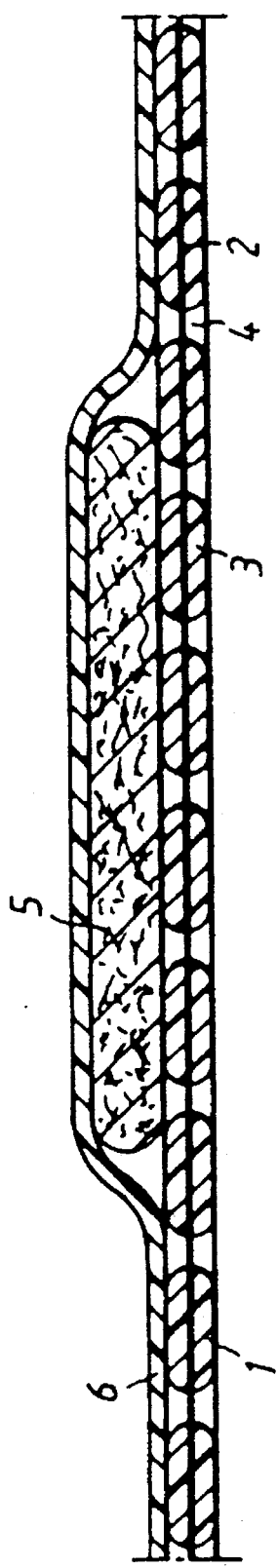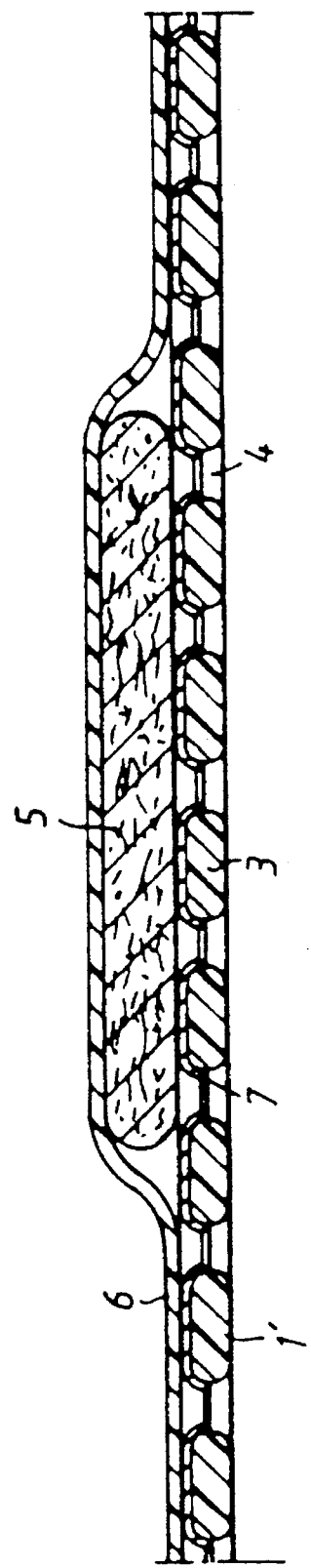

ABSORBENT WOUND DRESSING

This application is a 371 of PCT/SE93/00291, Mar. 30, 1993.

FIELD OF THE INVENTION

The present invention relates to an absorbent wound dressing comprising a layer of hydrophobic silicone gel which is intended to lie against the wound surface in use, a layer of carrier material which carries the gel layer and affords the requisite strength to said layer, and an absorbent body which is placed on that side of the carrier material and gel layer which lies distal from the wound surface in use, wherein the carrier material and the gel layer have mutually coinciding penetrating perforations at least within the region of the absorbent body.

BACKGROUND OF THE INVENTION

Applicant's European Patent No. 0,261,267 discloses a wound dressing which is comprised of a textile material that has been impregnated with silicone gel. The silicone gel may be comprised of a hydrophobic silicone gel of the same type as that used in the dressing Mepitel® retailed by Applicant. The patent specification mentions the possibility of using this wound dressing together with an absorbent body when the dressing is used for weeping wounds or sores. In order to ensure that the absorbent body will remain seated in the wound area in such applications, it is necessary to secure the body with a retaining layer after having applied the absorbent body to the wound, this retaining layer conveniently having the form of an elastic bandage. This use of Applicant's Mepitel® dressing is highly appropriate in the case of heavily weeping wounds or sores, when the absorbent body needs to be changed at given intervals, since the Mepitel® dressing can be left on the wound or sore during several absorbent body changes, which is particularly beneficial in the case of sensitive wounds. In the case of other applications, and particularly those applications when the entire dressing shall be removed after a given period of time, the aforesaid method of application can be experienced as troublesome and time-consuming. Furthermore, in the case of this kind of dressing, there is a risk that fluid from the wound will leak from the absorbent body and the retaining layer and fasten on the clothes of the person carrying the dressing. Furthermore, there is always a risk of infecting the wound when the dressing is removed.

SUMMARY OF THE INVENTION

The object of the present invention is to provide an absorbent wound dressing of the kind defined in the introduction which can be easily applied and which will fully eliminate, or at least greatly eliminate the risk of fluid leaking from the dressing.

In accordance with the invention, this object is achieved with an absorbent wound dressing of the aforedefined kind which is characterized by a fluid barrier layer on that side of the dressing which faces away from the wound surface when the dressing is in use, which fluid barrier layer is preshaped in the region of the absorbent body to a form which is complementary to the shape of the absorbent body projecting from the carrier-material and gel layers. Since the absorbent body is initially fastened to the remainder of the dressing, such a dressing can be applied much more easily than Applicant's known dressing, while preventing leakage at the same time and due to the preshape this will ensure that no tension or stresses remain in the fluid barrier layer subsequent to its application to the rest of the dressing, these tensions being otherwise difficult to avoid when the fluid barrier layer is shaped in conjunction with its application to the rest of the dressing and which can cause the dressing to curl at the edges thereof.

BRIEF DESCRIPTION OF THE DRAWINGS

The invention will now be described with reference to preferred embodiments of an absorbent wound dressing and also with reference to the accompanying drawings, in which FIG. 1 is a cross-sectional view of a first embodiment of an inventive absorbent wound dressing; and FIG. 2 is a cross-sectional view of a second embodiment of an inventive absorbent wound dressing.

DETAILED DESCRIPTION OF THE INVENTION

The wound dressing illustrated in FIG. 1 comprises a bottom sheet or layer 1 which lies against the wound surface and the surrounding healthy skin when the dressing is worn. This bottom layer is comprised of a textile material 2, for instance an elastic knitted net, which is impregnated with and encased in a hydrophobic silicone gel 3, while leaving penetrating holes 4. The silicone gel 3 is comprised of a two-component addition-hardening silicone gel, for instance the silicone gel obtained from Dow Corning and specified in the aforesaid European Patent No. 0,261,167, or the silicone gel sold by Wacker Chemie GmBH under the designation Wacker RTV-2, VP7612. A gel of this nature is soft, hydrophobic, self-adhesive and will adhere to dry skin, which renders it particularly suitable for use proximal to a wound or sore.

In addition to being soft, adhesive on dry skin, the silicone gels that can be used in the present invention are those which will not adhere to the wound or sore. The extremely low adhesion to wounds in comparison with other so-called non-adhesive dressings is achieved because the silicone gel has an extremely low surface tension and a surface chemistry which forms other types of adhesion forces against the wound surface than other polymers and metallic materials used in such dressings, wherein the force with which the silicone gel adheres to the wound surface is weaker than practically all of these polymeric and metallic materials. The silicone gel is also form-stable, i.e. it retains its original form when handled normally. Thus, there is no plastic deformation when the dressing lies against the wound, when the dressing is removed or when protective strips are removed from the gel surface, etc. The gel also obtains a very smooth and even surface in the process of manufacture, which also contributes to the low adhesion to the wound surface. The majority of other types of so-called non-adhering dressings have a larger available surface than the inventive dressing, as seen both macroscopically and microscopically, which results in stronger adhesion to the wound and to the dried wound fluid.

The strength at which the silicone gels used with the inventive dressing adhere to dry skin is considerably lower than the adhesive strength of those adhesives used with conventional self-adhesive tapes for securing wound dressings or for conventional self-adhesive wound dressings. The skin is thus protected from injury when removing the inventive dressing. One method of measuring this adhesive force is to stick 25 mm wide strips of an inventive dressing onto dry skin and to allow a weight attached to one end of the strip to draw the dressing gravitationally from the skin at an angle of 160° thereto. The weight which will draw the dressing from the skin at a speed of 1 mm/s can be determined with the aid of this test. The adherency measured in accordance with this test shall lie within the range of 5–200 g, preferably within the range of 20–60 g, in order to provide satisfactory adhesion and dressing peelability.

The hardness of the silicone gel is measured by means of a method in which a round steel rod having a flat end and a diameter of 9.2 mm is pressed into the gel to a depth of 5 mm. The force required is measured in the process. The hardness of a silicone gel suitable for use in an inventive dressing will lie in the range of 0.5–10N. An optical hardness value is 2N.

The penetrability of a silicone gel is measured with the aid of a method in which a conical test body is allowed to sink gravitationally into the silicone gel. The number of mm to which the test body has sunk over a period of 5 seconds constitutes the penetration value. The measurements were established with the aid of a cone obtained from Sommer & Runge AG and designated Petrotest Sommer & Runge 18–036.1, said cone being filled with glass spheres to a weight of 62.5 g. The penetration of a silicone gel that can be used in an inventive dressing will lie within the range of 5–20 mm. An optimal penetration value is 9 mm.

The tensile strength of a silicone gel was determined with the aid of a method in which a gel test strip was fastened vertically between two clamps, of which one could be moved at a constant speed. The strip was stretched until it fractured and the maximum force was recorded. The tensile strength of a silica gel that can be used in an inventive dressing will lie within the range of 1–8 N/10 mm in the case of a 3 mm thick strip, and preferably be 4 N/10 mm.

In addition to adhering to dry skin, the silicone gel will also adhere to other dry surfaces, and a good estimate of the adherence of the gel to dry skin can be obtained by measuring the force at which the gel adheres to a highly polished steel plate. The adherence of the silicone gel to a steel surface was determined by means of a method in which a test strip of silicone gel was applied to a steel plate and the strip then drawn from the plate with the withdrawn part of the strip being held at an angle of 90° thereto. The withdrawal or peeling force required was recorded. The adhesion force of a silicone gel that can be used in an inventive dressing measured in accordance with this method will lie within the range of 0.2–10 N/50 mm and will preferably be 2 N/50 mm.

An absorbent body 5 is placed on top of the textile material 1 impregnated with silicone gel. This body may be comprised of felt-type fibre material or of a textile material. The fibres may be normal textile fibres, such as cotton, rayon, etc., or may be comprised of special highly-absorbent fibres, such as alginate fibres or so-called superabsorbent fibres. The superabsorbent fibres may conveniently comprise bicomponent fibres with superabsorbents bonded to the surface of textile fibres.

That surface of the absorbent body 5 which lies proximal to the bottom layer 1 is conveniently treated with binder or heat so as to bind together the fibres in this surface, thereby greatly reducing the risk of fibres loosening from the absorbent body and finding their way into the wound or sore. Different wound-healing stimulating substances, such as NaCl and ZnO can be added to the absorbent body.

For the purpose of holding the absorbent body 5 firmly in place and preventing absorbed wound fluid leaking therefrom, the inventive wound dressing includes a fluid barrier layer 6 which covers the absorbent body and is secured to the bottom layer 1 at those parts thereof which lie outside the absorbent body. The fluid barrier layer is suitably comprised of a liquid-impermeable plastic film, for instance a polyethylene, polyamide or polyurethane film. It is also conceivable to use microporous materials which are not completely fluid-impervious but which allow fluid to diffuse through the material. Microporous materials have the advantage of providing better adhesion to the silicone gel in the layer 1, by presenting a greater adhesion surface to the gel. Furthermore, microporous materials enable the healthy skin to "breathe".

In order to ensure good adhesion when using plastic film as a fluid barrier layer, the film is suitably, but not necessarily coated with a silicone primer or silicone adhesive compound, for instance Dow Corning 355 Medical Adhesive.

When the fluid barrier layer is formed from an initially flat layer which is caused to take a shape complementary to the absorbent body when applying said layer to the unit consisting of said silicone-impregnated textile material and the overlying absorbent body, it is almost impossible to avoid the occurrence of stretch-tensions in the fluid barrier layer. It is highly probable that these stretch-tensions in a wound dressing that has been applied to a user will result in the edges of the dressing loosening from the skin or that the fluid barrier layer will be delaminated from the silicone-impregnated textile material 1, starting from the edges of the dressing. Accordingly, in order to avoid such risks, the fluid barrier layer 6 is pre-formed in the region of the absorbent body 5 to a shape which is complementary to said body. The fluid barrier layer may be pre-formed by vacuum-shaping said layer while applying heat, or by some other stretch-shaping method under the application of heat. In addition to avoiding the risk of delamination or edge-curling, pre-forming of the fluid barrier layer also avoids the formation of folds in said layer when the layer is applied to the unit consisting of the absorbent body and underlying silicone-gel-impregnated textile material.

If the absorbent body 5 swells to a pronounced extent when absorbing wound fluid, for instance when the body contains superabsorbents, the fluid barrier layer is preferably given a form which is complementary to the form of a swollen absorbent body, i.e. the form taken by the body when saturated with absorbed wound fluid.

FIG. 2 illustrates a second embodiment of an inventive wound dressing. Those components which are similar to the components of the dressing shown in FIG. 1 have been identified by the same reference signs. The wound dressing illustrated in FIG. 2 differs from the wound dressing illustrated in FIG. 1 in that the bottom layer 1' is not comprised of a silicone-gel-impregnated textile material, but instead consists in a perforated carrier material 7 to which a layer of silicone gel 3 has been applied. The carrier material is comprised totally or essentially of plastic film which is impervious to air and fluid or a microporous material, e.g. a Gore-Tex® type material. A method of manufacturing a bottom layer of this kind is described in our Swedish Patent Application No. 9200983-6 filed on the same day as the present application and to which reference is made for more detailed disclosures concerning the construction of the bottom layer 1'. One advantageous afforded by the bottom layer described with reference to FIG. 2 is that the fluid barrier layer can be fastened to said bottom layer more easily than to the bottom layer described with reference to FIG. 1.

It will be understood that the described and illustrated embodiments of an inventive wound dressing can be modified within the scope of the invention, particularly with regard to the materials used for the dressing components. For instance, the absorbent body may include any wound fluid-absorbing material whatsoever, fluid-impervious plastic films other than those described can be used without departing from the concept of the invention. The invention is therefore limited solely by the content of the following Claims.

I claim:

1. In an absorbent wound dressing comprising a layer of hydrophobic silicone gel (3) which is intended to lie against the wound surface when the dressing is worn, a layer of carrier material (2; 7) which supports the gel layer and which affords the necessary strength to said gel layer, and an absorbent body (5) which is placed on that side of the carrier material and gel layer which lies distal from the wound surface in use, wherein the carrier material and gel layer have mutually coinciding penetrating perforations (4) at least within the region of the absorbent body, the improvement wherein a fluid barrier layer (6) is provided on that side of the dressing which lies distal from the wound surface in use and wherein within the region of the absorbent body (5), the fluid barrier layer (6) is preshaped to a form which is complementary to the form of the absorbent body projecting out from the layers of carrier material (2; 7) and gel layer.

2. An absorbent wound dressing according to claim 1, wherein the fluid barrier layer (6) is preshaped to a form which is complementary to the absorbent body subsequent to said body being saturated with absorbed wound fluid.

3. An absorbent wound dressing according to claim 1, wherein the fluid barrier layer (6) is selected from the group consisting of a fluid-impervious plastic film, and a microporous material.

4. An absorbent wound dressing according to claim 1, wherein the fluid barrier layer (6) is coated with a silicone primer on that side which faces towards the silicone-gel carrier-material (2; 7).

5. An absorbent wound dressing according to claim 1 wherein the carrier material is comprised of a textile material (2) that has been impregnated with silicone gel (3).

6. An absorbent wound dressing according to claim 1, wherein the carrier material is comprised of a totally or essentially air-impervious and fluid-impervious perforated layer material (7) to which a layer (3) of silicone gel is adhered.

* * * * *